United States Patent [19]

Witkowski et al.

[11] Patent Number: 4,963,261
[45] Date of Patent: Oct. 16, 1990

[54] MICROPOROUS MEMBRANE HAVING A MACROPOROUS SUPPORT

[75] Inventors: Gregory Witkowski, Greenpoint; Bamdad Bahar, New York; Irving M. Wolbrom, Great Neck, all of N.Y.

[73] Assignee: Chromex Corp., Brooklyn, N.Y.

[21] Appl. No.: 399,603

[22] Filed: Aug. 28, 1989

[51] Int. Cl.$^5$ .............................................. B01D 69/12
[52] U.S. Cl. .................................... 210/490; 427/245; 210/500.27; 210/496
[58] Field of Search ............... 210/450, 445, 446, 486, 210/496, 321.75, 321.84, 490, 500.25, 500.26, 500.27; 427/245, 246

[56] References Cited

U.S. PATENT DOCUMENTS 3,441,143  4/1969  Kudlaty ........................ 210/486 X
3,464,562  9/1969  Meyers et al. ................. 210/486 X
3,494,465  2/1970  Nyrop ........................... 210/486 X Primary Examiner—Frank Spear
Attorney, Agent, or Firm—Alan H. Levine

[57] ABSTRACT

A porous structure comprising a macroporous support and a microporous membrane adhered to the outside surface of the support. Each of the support and membrane may be formed of a synthetic polymer, the polymers of the support and membrane usually being different from each other. The structure is formed by placing the membrane and a quantity of heat-fusible particles in contact with each other, and subjecting the membrane and particles to heat and pressure to fuse the particles into a macroporous support. The melting point of the membrane material should be no lower than that of the particle material.

12 Claims, 1 Drawing Sheet

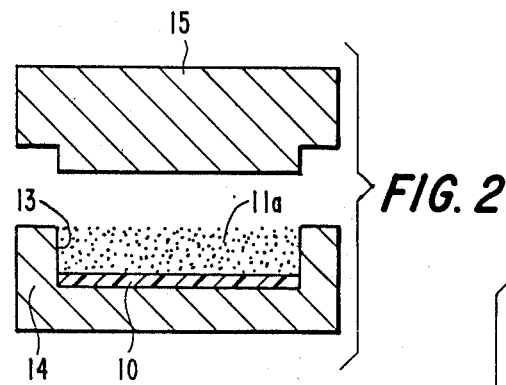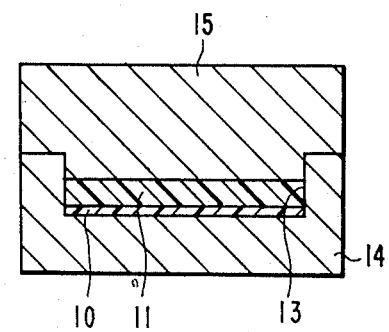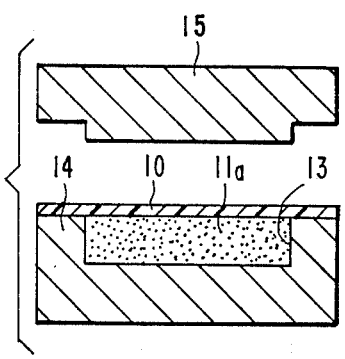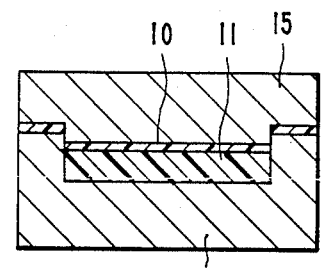

MICROPOROUS MEMBRANE HAVING A MACROPOROUS SUPPORT

This invention relates to porous structures and more particularly to structures involving microporous membranes.

Microporous membranes, usually made of synthetic polymers, have many uses, probably the most important of these being in the field of filtration. A problem presented by microporous membranes, because they are very thin, is that they are not self-supporting and have low structural strength. Thus, for example, they cannot tolerate high pressure gradients since they are subject to tearing when stressed too greatly. Also, the membranes are somewhat difficult to handle.

One approach to solving these problems is found in U.S. Pat. No. 4,761,232. That patent describes a porous structure comprising a macroporous substrate, the pores of the substrate being filled with a microporous material. The disadvantage of this product is that its manufacture involves a number of complications, and it does not provide for use of commercially available thin microporous membranes.

It is an object of the present invention to provide a porous structure incorporating a preexisting microporous membrane, the membrane being supported by a macroporous support or substrate.

It is another object of the invention to provide such a porous structure wherein the macroporous support is formed, and the membrane adhered to it, in a single step. To achieve this objective, a microporous membrane is placed in contact with a quantity of heat-fusible particles, the membrane and particles being subjected to heat and pressure to fuse or sinter the particles into a macroporous support and cause the membrane to adhere to the support.

According to this invention, the membrane contacts only an outside surface of the support, and does not penetrate into the pores of the support. This distinguishes from the product of the patent mentioned above wherein the microporous material fills the pores of the macroporous substrate and must be formed in situ from a solution of the polymer of which the microporous material is made.

Additional objects and features of the invention will be apparent from the following description in which reference is made to the accompanying drawings.

In the drawings:

FIG. 1 is a schematic illustration of a porous structure according to this invention;

FIG. 2 is a schematic illustration of a membrane and heat-fusible particles in a mold, the mold being open;

FIG. 3 is a view similar to FIG. 2, but with the mold closed.

FIG. 4 is a schematic illustration of an alternative arrangement of particles and membrane in a mold, the mold being open; and FIG. 5 is a view similar to FIG. 4, but with the mold closed.

The porous structure chosen to illustrate the present invention, and shown in FIG. 1, comprises a microporous membrane 10 adhered to a face of a macroporous support 11. As used herein, the term microporous means having pores which are less than 10 microns in diameter, and the term macroporous means having pores greater than 10 microns in diameter.

Microporous membranes 10 with which the present invention is useful have thicknesses of 20 mils or less. The shape and thickness of support 11 will depend upon the particular end use for the porous structure, i.e., usually the product with which the structure is to be used will dictate the size and shape of the support, as well the shape of the membrane.

The porous structure is made by placing a microporous membrane 10 at the bottom of the cavity 13 in a mold part 14 (FIG. 2). Then, a quantity of heat-fusible particles 11a is poured over the membrane to substantially fill the remainder of the cavity 13. Thereafter, another mold part 15 is brought into engagement with mold part 14 (FIG. 3) to close the mold and compress the articles against one another and against membrane 10. The mold is heated sufficiently to cause the particles to fuse together into an integral unit, while leaving, a labyrinth of interconnected macropores throughout the fused body. The mold is opened and the porous structure comprising the support 11 carrying the membrane 10 is removed from the mold.

The melting point of the membrane material should be no lower than that of the support material s that the membrane will not melt at the fusing temperature of the particles. Even some melting of the membrane could result in some loss of porosity due to closing of the micropores. However, since the particles become tacky at their fusing temperature, the particle material actually serves as an adhesive for bonding the membrane to the support, this bonding being aided by the pressure of the particles against the membrane when the particles and membrane are compressed in the mold before, during, or after heating.

Preferably, each support 11 and membrane 10 is formed of a synthetic polymer. Examples of the polymers useful for making the support are polyethylene, polypropylene, polyester, ethylene vinyl acetate, nylon, polysulfone, polyvinylidene fluoride, and polytetrafluoro ethylene. Typical membrane materials used to make commercially available microporous membranes, are nylon, nitrocellulose, polycarbonate, polysulfone, polyvinylidene fluoride, and polyethylene. Usually, the material of the support will be different from that of the membrane, so that a support material can be chosen having a lower melting point than that of the membrane material.

However, particles 11a and membrane 10 of the same material could be used if the temperatures are different at different parts of the mold. For example, in some circumstances mold part 15 will be hotter than mold part 14, so that membrane 10 will not melt although sufficient heat is furnished to fuse particles 11a.

Depending upon the material of the particles used to make the support 11, the mold 14, 15 will be heated to the temperature needed to fuse those particles. Generally, temperatures between 175° F. and 700° F. will be employed. The particles selected to make the support are of a size such that upon being fused together, they leave macropores between them of the desired size. Generally, the particles will have an average diameter between about 20 and 1000 microns. If the particles are smaller than 20 microns, interconnected macropores may not be reliably produced. If the particles are larger than 1000 microns, the resulting pores in the support may exceed capillary size.

It has been found that application of some pressure to the particles and membrane during the heating and fusing step insures a good bond between the membrane and the final support. Appropriate pressures, produced by the closed mold parts (FIG. 3) are those which reduce the initial volume of the particles from between 10% and 60%. In the words, the volume of the particles in the closed mold, shown in FIG. 3, should be 90% to 40% of the volume of the particles in the open mold prior to fusing, as shown in FIG. 2. Regardless of the pressure used, the membrane 10 of the resulting porous structure engages only an outer surface of the support 11. Since the membrane does not melt, it does not flow into the pores of the support.

An alternative method of making the porous structure is illustrated in FIGS. 4 and 5. The only difference between this method and that shown in FIGS. 2 and 3 is that the particles 11a are placed in the mold cavity 13 before the membrane (FIG. 4). Thereafter, the membrane 10 is placed on top of the particles, and the mold is closed (FIG. 5).

If desired, additional particulate or liquid materials can be mixed with the particles 11a depending upon the end use of the porous structure. Examples of such additives are surfactants to aid wettability, glass beads to reduce weight, electrically-conductive materials, colorants, and flame retardants.

Porous structures according to this invention have many possible uses. For example, in the field of filtration, the microporous membrane 10 can filter out bacteria and viruses from a fluid, the support 11 carrying the membrane making for a unit which can be handled easily for replacement or cleaning. The macroporous support can serve as a reservoir from which a product can be released in a controlled manner through the membrane; a transdermal drug delivery system is an example of such use.

In the field of diagnostics, antibody coated latex particles can be entrapped on the membrane surface while all the solutions are absorbed by the support. Due to the capillarity of the support, it can actually enhance the performance of the membrane. Thus, if some liquid starts to pass through the membrane, the capillary action of the support helps to pull the liquid through the membrane.

The invention has been shown and described in preferred form only, and by way of example, and many variations may be made in the invention which will still be comprised within its spirit. It is understood, therefore, that the invention is not limited to any specific form or embodiment except insofar as such limitations are included in the appended claims.

We claim:

1. A porous structure comprising
   a macroporous support, and
   a microporous membrane in contact with an outs surface of the support,
   the structure being formed by placing a preexist membrane in contact with a quantity of discr polymer particles, and heat fusing the partic together to form the support, the membrane maining in contact with the particles while latter are fused together.

2. A porous structure as defined in claim 1 wher each of the support and membrane is formed of a s thetic polymer.

3. A porous structure as defined in claim 2 wher the synthetic polymer forming the support is differ from the synthetic polymer forming the membrane.

4. A porous structure as defined in claim 2 wher the synthetic polymer forming the support is the sa as the synthetic polymer forming the membrane.

5. A method of making a porous structure compris the steps of:
   providing a preexisting microporous membrane,
   providing a quantity of discrete, heat-fusible pa cles,
   placing the membrane and quantity of particles contact with each other and
   subjecting the membrane and particles to a temp ture sufficient to fuse the particles into a macro rous support to which the membrane is adhere 6. A method as defined in claim 5 wherein each of support and membrane is formed of a synthetic p mer.

7. A method as defined in claim 5 wherein the melt point of the membrane material is higher than tha the particle material.

8. A method as defined in claim 5 wherein the m brane and particles are subjected to pressure as wel elevated temperature to fuse the particles together adhere the membrane to an outside surface of the fu together particles.

9. A method as defined in claim 5 wherein the m brane has a thickness no greater than 20 mils.

10. A method as defined in claim 5 wherein the pa cles have an average size between 20 and 1000 micr 11. A method as defined in claim 5 wherein prio subjecting the membrane and particles to the fu temperature, the particles are placed in a mold and membrane placed on the exposed upper surface of particles.

12. A method as defined in claim 5 wherein prio subjecting the membrane and particles to the fu temperature, the membrane is placed in a mold and particles placed on top of the membrane.

* * * * *